(12) United States Patent  
Keady

(10) Patent No.: US 9,216,237 B2
(45) Date of Patent: Dec. 22, 2015

(54) ELECTROACTIVE POLYMER SYSTEMS

(71) Applicant: Personics Holdings, LLC., Boca Raton, FL (US)

(72) Inventor: John P. Keady, Fairfax Station, VA (US)

(73) Assignee: Personics Holdings, LLC, Boca Raton, FL (US)

( * ) Notice: Subject to any disclaimer, the term of this patent is extended or adjusted under 35 U.S.C. 154(b) by 0 days.

(21) Appl. No.: 14/246,696

(22) Filed: Apr. 7, 2014

(65) Prior Publication Data

US 2014/0216480 A1 Aug. 7, 2014

Related U.S. Application Data

(63) Continuation of application No. 12/268,195, filed on Nov. 10, 2008, now Pat. No. 8,718,313.

(60) Provisional application No. 60/986,606, filed on Nov. 9, 2007.

(51) Int. Cl.
*H04R 25/00* (2006.01)
*A61L 31/04* (2006.01)
*H04R 17/00* (2006.01)
*A61F 11/08* (2006.01)
*A61L 31/14* (2006.01)
*H04R 1/10* (2006.01)

(52) U.S. Cl.
CPC ............ *A61L 31/04* (2013.01); *A61F 11/08* (2013.01); *A61L 31/14* (2013.01); *H04R 17/00* (2013.01); *H04R 25/652* (2013.01); *A61L 2400/00* (2013.01); *H04R 1/10* (2013.01); *H04R 25/00* (2013.01); *H04R 2460/15* (2013.01); *H04R 2499/11* (2013.01); *Y10T 428/249953* (2015.04)

(58) Field of Classification Search
CPC ...... A61L 2400/00; A61L 31/04; A61L 31/14; A61F 11/08; H04R 2460/15; H04R 2499/11; H04R 1/10; H04R 25/00
See application file for complete search history.

(56) References Cited

U.S. PATENT DOCUMENTS 4,962,537 A  10/1990  Basel et al.
5,333,622 A   8/1994  Casali et al.
5,483,027 A   1/1996  Krause
(Continued)

FOREIGN PATENT DOCUMENTS

JP    9-312984    12/1997
WO    WO 96-11521   4/1996

OTHER PUBLICATIONS

Machine translated document (JP 9-312984).

*Primary Examiner* — A. Sefer
(74) *Attorney, Agent, or Firm* — Pablo Meles

(57) ABSTRACT

A device includes a core, a membrane, at least one first electrode coupled to the core, at least one second electrode coupled to the core or the membrane and a collapsible electroactive polymer element. The collapsible polymer element is configured to extend from or extend around at least a portion of the core where the element is in an expanded configuration without application of a voltage and in a collapsed configuration with the application of the voltage or in a collapsed configuration without application of a voltage and in an expanded configuration with the application of the voltage. The voltage is applied via the at least one first electrode and the at least one second electrode. Other embodiments are disclosed.

15 Claims, 3 Drawing Sheets

(56) References Cited

U.S. PATENT DOCUMENTS

| | | |
|---|---|---|
| 6,094,494 A | 7/2000 | Haroldson |
| 6,249,076 B1 | 6/2001 | Madden et al. |
| 6,256,396 B1 | 7/2001 | Cushman |
| 6,632,215 B1 | 10/2003 | Lemelson |
| 7,164,775 B2 | 1/2007 | Meyer et al. |
| 7,362,875 B2 | 4/2008 | Saxton et al. |
| 7,387,187 B2 | 6/2008 | Widmer et al. |
| 7,732,999 B2 | 6/2010 | Clausen et al. |
| 7,766,893 B2 | 8/2010 | Thomas |
| 7,834,527 B2 | 11/2010 | Alvarez Icaza Rivera et al. |
| 7,922,740 B2 | 4/2011 | Eidenschink et al. |
| 2002/0054060 A1 | 5/2002 | Schena |
| 2002/0122561 A1 | 9/2002 | Pelrine et al. |
| 2002/0130673 A1 | 9/2002 | Pelrine et al. |
| 2003/0023270 A1 | 1/2003 | Danz et al. |
| 2005/0122007 A1 | 6/2005 | Ishibashi et al. |
| 2006/0113878 A1 | 6/2006 | Pei et al. |
| 2007/0118169 A1 | 5/2007 | Eidenschink et al. |
| 2007/0152974 A1 | 7/2007 | Kim et al. |
| 2007/0159031 A1 | 7/2007 | Yokoyama et al. |
| 2007/0219576 A1* | 9/2007 | Cangialosi .................... 606/198 |
| 2007/0250036 A1* | 10/2007 | Volk et al. .................... 604/510 |
| 2008/0061518 A1 | 3/2008 | Gilliland et al. |
| 2008/0083314 A1 | 4/2008 | Hayashi et al. |
| 2008/0132749 A1 | 6/2008 | Hegde et al. |
| 2008/0299339 A1 | 12/2008 | Keady |
| 2009/0085444 A1* | 4/2009 | Alvarez Icaza Rivera et al. .................... 310/365 |
| 2009/0103763 A1* | 4/2009 | Petef et al. .................... 381/380 |
| 2010/0211186 A1 | 8/2010 | Senders et al. |
| 2011/0017829 A1 | 1/2011 | Wang et al. |
| 2011/0066091 A1 | 3/2011 | Larson et al. |
| 2011/0169742 A1 | 7/2011 | Lipton et al. |

\* cited by examiner

ELECTROACTIVE POLYMER SYSTEMS

CROSS-REFERENCE TO RELATED APPLICATIONS

This application is a continuation of and claims the benefit of U.S. patent application Ser. No. 12/268,195 filed on 10 Nov. 2008 and further claims the benefit of U.S. provisional patent application No. 60/986,606 filed on 9 Nov. 2007, the disclosures of which are both incorporated herein by reference in their entirety.

FIELD

The present invention relates to sealing devices and more particularly, though not exclusively, to earpiece devices using electroactive, force responsive, or inflatable systems.

BACKGROUND

Various earpieces (e.g. headphones, earbuds, behind the ear, hearing aids, and other devices that direct acoustic energy into an acoustic measuring device (e.g., ear)) have been designed for various uses. Many conventional systems have difficulty sealing in the ear canal. Custom fitting is used in the hearing aid industry by taking a mold of the subjects ear canal, and then designing a device which fits closely to the mold. There are issues with sealing since the ear canal changes in time, and the cost and time involved with just efforts.

SUMMARY

At least one exemplary embodiment is directed to a device comprising a membrane and a collapsible electroactive polymer element, wherein the element is in an expanded configuration without voltage application and is in a collapsed configuration with a voltage application, and where the element is covered by the membrane. The electroactive polymer element can be a gel. The electroactive polymer element can be an electroactive polymer that bends about a point when a voltage is applied across the electroactive polymer. The membrane can reduce any water in the electroactive polymer element from passing through the membrane to the environment. The membrane can include additional straightening folds to reduce membrane resistance to bending.

At least one exemplary embodiment is directed to a device where the electroactive polymer element includes: a first electroactive polymer sub element; a second electroactive polymer sub element; a first sub electrode operatively connected to the first electroactive polymer sub element; a second sub electrode operatively connected to the first and second electroactive polymer sub elements; a third sub electrode operatively connected to the second electroactive polymer sub element, where a first voltage difference between the first sub electrode and the second sub electrode and a second voltage difference between the second sub electrode and third sub electrode results in movement of a portion of the first and second electroactive polymer sub elements in the same direction.

At least one exemplary embodiment is directed to a sealing device, comprising: at least one electroactive polymer element; a core; a first electrode; and a second electrode, where the at least one electroactive polymer element forms a flange shape, where the flange shape moves toward the core when voltage is applied between the first and second electrodes.

At least one exemplary embodiment is directed to a sealing device, comprising: a moment arm; an electroactive polymer element; a first electrode; a second electrode; and a core, where a first end of the electroactive polymer element is operatively attached to the core and a second end of the electroactive polymer element is operatively attached to the moment arm, where the moment arm is operatively attached at a position along the core so that the moment arm can rotate about the position where the first electrode is operatively connected to a first side of the electroactive polymer element and the second electrode is operatively attached to a second side of the electroactive polymer element so that when a voltage difference is applied between the first and second electrodes the moment arm is rotated about the position.

Further areas of applicability of exemplary embodiments of the present invention will become apparent from the detailed description provided hereinafter. It should be understood that the detailed description and specific examples, while indicating exemplary embodiments of the invention, are intended for purposes of illustration only and are not intended to limit the scope of the invention.

BRIEF DESCRIPTION OF THE DRAWINGS

Exemplary embodiments of present invention will become more fully understood from the detailed description and the accompanying drawings, wherein.

DETAILED DESCRIPTION OF EXEMPLARY EMBODIMENTS

Figure 1:
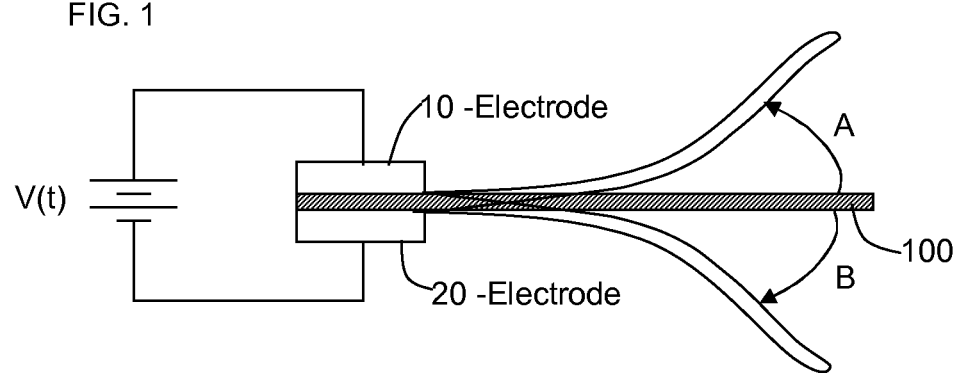
FIG. 1 illustrates an IPMC configuration.

The following description of exemplary embodiment(s) is merely illustrative in nature and is in no way intended to limit the invention, its application, or uses.

Exemplary embodiments are directed to or can be operatively used on various wired or wireless earpieces devices (e.g., earbuds, headphones, ear terminals, behind the ear devices or other acoustic devices as known by one of ordinary skill, and equivalents).

Processes, techniques, apparatus, and materials as known by one of ordinary skill in the art may not be discussed in detail but are intended to be part of the enabling description where appropriate. For example specific materials may not be listed for achieving each of the targeted properties discussed, however one of ordinary skill would be able, without undo experimentation, to determine the materials needed given the enabling disclosure herein. Such code is intended to fall within the scope of at least one exemplary embodiment.

Additionally exemplary embodiments are not limited to earpieces, for example some functionality can be implemented on other systems with speakers and/or microphones for example computer systems, PDAs, BlackBerry® smart phones, cell and mobile phones, and any other device that emits or measures acoustic energy. Additionally, exemplary embodiments can be used with digital and non-digital acoustic systems. Additionally various receivers and microphones can be used, for example micro-electro-mechanical systems (MEMs) transducers, diaphragm transducers, for example Knowles' FG and EG series transducers.

Notice that similar reference numerals and letters refer to similar items in the following figures, and thus once an item is defined in one figure, it may not be discussed or further defined in the following figures.

Exemplary Embodiments

Note when discussing a sealing section or a device that seals, such a section or device can use various materials (e.g., viscosity varying polymers), for example polymers that are liquid at one temperature then gel at another, or switch between a gel and liquid with pH, current, pressure, or any other variation in energy, or any other similar material as known by one of ordinary skill in the relevant arts. For example the following is a non-limiting list of references that discuss materials that can be used: U.S. Pub. No. 2002/0168319; U.S. Pat. Nos. 6,660,247; 6,352,682; 6,113,629; 6,090,911; 5,976,648; 5,942,209; 5,939,485; 5,876,741; 5,858,746; 5,843,156; 5,766,704; 5,749,922; 5,702,361; 5,695,480; 5,674,287; 5,662,609; 5,634,946; 5,589,568; 5,575,815; 5,525,334; 5,514,379; 5,410,016; 5,256,765; 5,252,318; 5,213,580; 6,660,247; and 4,732,930. Additionally electroactive polymers can be utilized for example electroactive gels, IPMCs, basically any polymer that changes shape (contracts, expands, or bends) in response to a voltage difference across the polymer (e.g., Nafion™ based IPMCs).

Additionally, the fillable material referred to herein can also be viscous and can include silicone-based polymers, gels, vinyl elastomers, or any other material of sufficient properties to allow the deformation of a membrane cavity from user contact. Materials can also be used to provide a slow reformation of the original membrane cavity shape after it has been deformed and released. In this regard, a silicone gel or other non-cross-linked polymer or uncatalyzed materials may be used. It should be appreciated that the composition of the fillable material could be altered for applications in which varied membrane characteristics are desired (i.e. more stiffness, durability, more or less deformability and/or longer-lasting deformation). The fillable material can be elastically deformed or it may be deformed by displacement, which is the actual movement or flow of the fillable material in response to pressure, such as that from a user's fingertips. In addition, the fillable material could be altered for applications in which varied temperature or light conditions would be encountered during the use of particular products on which the membrane cavity is mounted.

If a membrane is used, a portion of a membrane connected to a structure (base membrane) can be made of any material, rigid or elastic, including various plastic or metal materials, or it can be made of a membrane formed of thin rubber-based material, deformable plastic or silicone-based materials or other elastomeric materials suitable for a given application. If the base is configured as a flexible membrane, the cavity can more easily conform to a product's surface, thereby increasing the ease with which the cavity can be installed, removed, and replaced. Likewise, the outer membrane also can be made of a thin rubber-based material, deformable plastic or silicone polymer materials, or other elastomeric materials suitable for a given application. If the base membrane and outer membrane are made of silicone material, both should be from 0.1 mm to 2.5 mm in thickness. In this regard, the base may be a membrane instead of a piece of rigid material. The edges of the outer membrane and the base membrane can be mechanically fastened or clamped forming the membrane cavity. Additionally, at least a portion of the base membrane can be adhesively attached (e.g., adhesive tape, glue) or mechanically fastened to the support structure.

The silicone sealant can be of an acetoxy cure type. In particular, upon exposure to moisture, the silicone sealant will give off small amounts of acetic acid while the sealant cures. The sealant will cure in 24 hours and has a tack free time of 10-20 minutes at 77.degree. F. (25.degree. C.) with 50% relative humidity. The sealant's tensile strength is approximately 350 psi, its elongation property is 450%, and its hardness is approximately 25-30 Shore A. The sealant has temperature stability from −85.degree. F. to 450.degree. F. (−65.degree. C. to 232.degree. C.) and can withstand intermittent exposure to temperatures as high as 500.degree. F. (280.degree. C.). The sealant is believed to have good resistance to various weathering conditions, including UV radiation, rain, snow, etc, without hardening, cracking, or shrinking.

For optimum adhesion with the above adhesive, the support structure and the lower surface of the base membrane should be clean, dry, and free from oil, grease or other foreign material. If necessary, metal surfaces should be wiped with a non-oily solvent. Rubber surfaces should be abraded to promote adhesion. Depending on environmental conditions, the base and product surface should be joined within 5-10 minutes, before the tack-free time of the sealant passes.

Note that various materials have been discussed, all forms of electroactive polymers can be used. For example Electroactive polymers (EAPs) are touted as the basis for future artificial muscles. EAPs can be deformed repetitively by applying external voltage across the EAP, and they can quickly recover their original configuration upon reversing the polarity of the applied voltage.

Artificial muscle polymers can be formed from a conductive polymer doped with surfactant molecule or from an ionic polymer metal composite (IPMC). Doped electroactive polymers (EAPs) are conductive polymers (e.g., polypyrrole or polyanaline) doped with a surfactant (e.g., sodium dodecyl benzene sulfonate). IPMCs typically consist of perfluorsulfonate polymers that contain small proportions of sulfonic or carboxylic ionic functional groups. Nafion®, a polymer made by DuPont, is one example of a poly(tetrafluoroethylene) based ionomer. For its application as an artificial muscle, Nafion® can be produced in a sheet geometry with positive counter ion (e.g., Na+ or Li+) contained in the matrix. The outer surface region (less than a micrometer) of the polymer sheet is then impregnated with a conductive metal such as platinum or gold. The resulting EAP polymer can absorb water until its physical ability to expand is balanced by the affinity of water for the polymer-fixed ions and free counter ions. When an electrical field is applied across the EAP, the EAP deforms as a result of stresses generated by the movement of water and mobile positive ions in the polymer composite. Additional applicable materials are electronic EAPs and Ionic EAPs. For example ferroelectric polymers, dielectric EAPs, electrostrictive graft elastomers, electrorestrictive paper, electro-viscoeleastic elastomers, liquid crystal elastomer materials, ionic polymer gels, ionomeric polymer metal composite (IPMC), conductive polymers, carbon nanotubes and other similar materials as known by one of ordinary skill in the arts.

Note that many of the sizes of the earpieces can vary so that an earpiece is about 10s of mm in diameters, and 10s mm in length, with a mass varying from 5 grams to hundreds of grams. For example sealing sections can be in the minimal compressed dimension roughly 7 mm (ring diameter), whereas in the uncompressed dimension can be 14 mm (ring diameter). For example at least one exemplary embodiment has a non deformable core diameter of about 5 mm with a length of about 25 mm, with an additional surrounding deformable lay (e.g., sealing section) of an additional 5 mm on either side of the core. The instrument package can be roughly a cylinder of length 10 mm and diameter of about 14 mm.

Note that although an earpiece is described herein, other devices that can use various viscosity polymers or sealing elements are also meant to fall within the scope of at least one exemplary embodiment of the present invention, for example a drain plug, a pipe plug, a device for sealing the pipe up to a design pressure at which the gel will liquefy and be released or other sealing or impact type situations.

FIG. 1 illustrates an IPMC that has electrodes (10 and 20) on either side of the IPMC (100). Varying the voltage V(t) causes deflection (e.g., bending, expansion, contraction, movement) of the electroactive polymer element (e.g., 100, 230, 340, 440, 530) in various directions (e.g., A and B).

Figure 2:
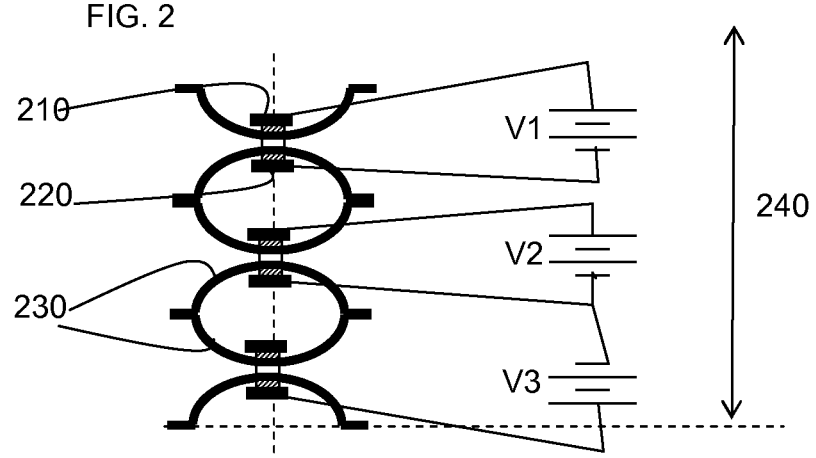
FIG. 2 illustrates a device in accordance with at least one exemplary embodiment.

FIG. 2 illustrates a sealing device in accordance with at least one exemplary embodiment where electroactive polymer elements (e.g., 230) operatively connected to electrodes (e.g., electrode 210 and electrode 220) are attached to each other so that when a voltage is applied (e.g., V1, V2, V3) the sealing device moves (e.g., 240). Note that electrodes 210, 220 can share the same voltage, for example V2 and V3. Thus the voltage differences across electrodes 210, 220 can be alternated so that the net voltage difference is not large. For example if the voltage difference is 5 volts, then alternating the voltage difference from −V to +V can keep the net voltage difference lower than 5V+5V+5V across the entire sealing device. For example electroactive gels will contract or expand when a voltage difference is applied, however either electrode 210, 220 can be the lower voltage, thus alternating electrodes in this manner can be used to move sub units of electroactive polymers without increasing the needed net voltage difference.

Figure 3:
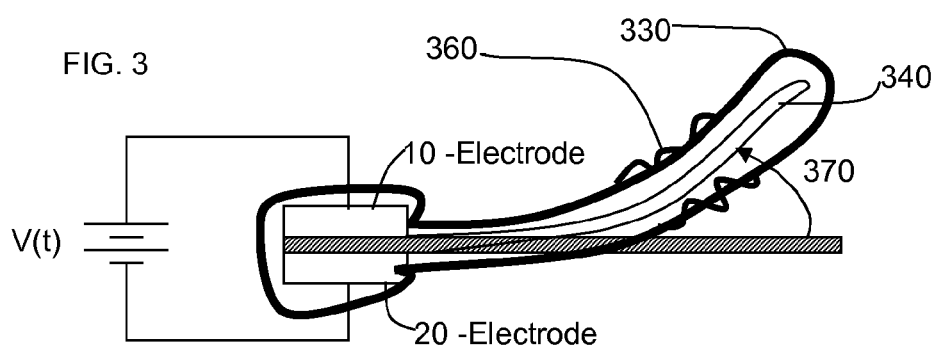
FIG. 3 illustrates another device in accordance with at least one exemplary embodiment.

FIG. 3 illustrates at least one exemplary embodiment comprising a device comprising: a membrane 330; and a collapsible electroactive polymer element 340 (e.g. element 530 in FIG. 5), wherein the element 340 is in an expanded configuration without voltage application and is in a collapsed configuration with a voltage application, where the element 340 is covered by the membrane 330. The electroactive polymer element 340 can be any material discussed or known that reacts to an applied voltage, current, pH level. Note that the membrane 330 can include additional straightening folds (360) to reduce membrane resistance to bending (370).

Figure 4:
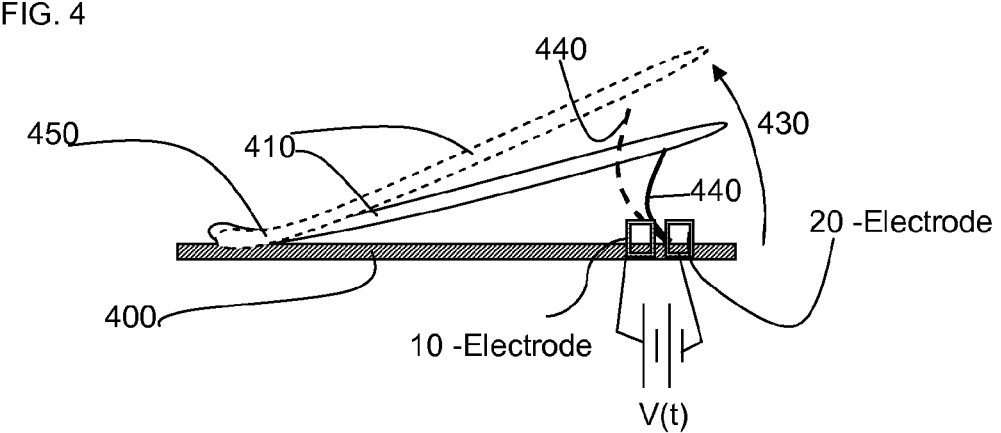
FIG. 4 illustrates a device in accordance with at least one exemplary embodiment.

FIG. 4 illustrates a moment arm 410 that pivots 430 about a point 450 when an electroactive polymer 440 has a voltage applied V(t) between two electrodes (10, 20). The moment arm can be attached to a core 400 (e.g., an acoustic tube). The electroactive polymer elements 440 can be flexibly attached to the moment arm so that application of a voltage difference across sides can result in straightening of the electroactive polymer element 440 thus translating into a rotation of the moment arm 410. Note the moment arm 410 can be any material (solid, membrane, flexible rigid, or any material already discussed).

Figure 5:
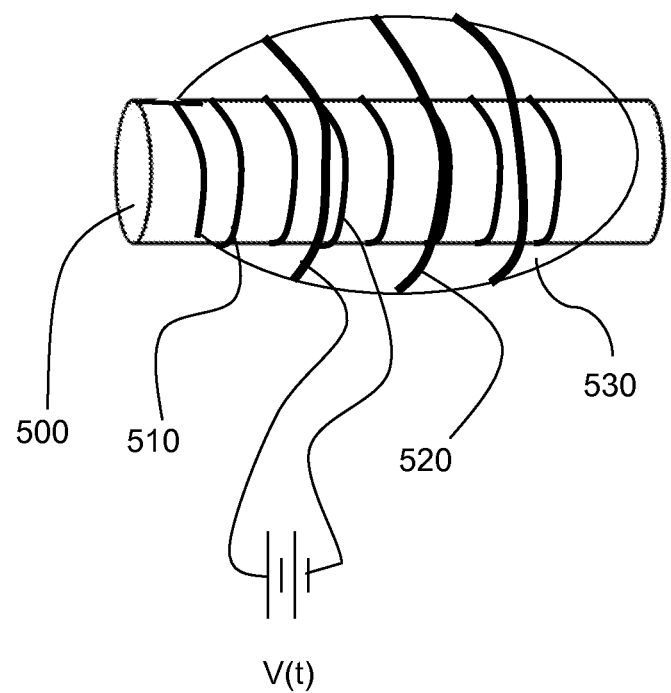
FIG. 5 illustrates another device in accordance with at least one exemplary embodiment.

FIG. 5 illustrates a sealing device that includes a core 500 with a first set of electrodes 510, a membrane containing (or the surface of) an electroactive polymer element 530, where the membrane and/or surface contains a second set of electrodes 520. When a voltage is applied across the electrodes 510, 520 the electroactive polymer element 530 can expand or contract in a radial direction away or to the core 500.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions of the relevant exemplary embodiments. For example, if words such as "orthogonal", "perpendicular" are used the intended meaning is "substantially orthogonal" and "substantially perpendicular" respectively. Additionally although specific numbers may be quoted in the claims, it is intended that a number close to the one stated is also within the intended scope, i.e. any stated number (e.g., 20 mils) should be interpreted to be "about" the value of the stated number (e.g., about 20 mils).

Thus, the description of the invention is merely exemplary in nature and, thus, variations that do not depart from the gist of the invention are intended to be within the scope of the exemplary embodiments of the present invention. Such variations are not to be regarded as a departure from the spirit and scope of the present invention.

What is claim is:

1. A device comprising:
    a core;
    a membrane;
    at least one first electrode connected to the core;
    at least one second electrode connected to the membrane;
    a collapsible electroactive polymer element configured to extend from or extend around at least a portion of the core, wherein the element is in an expanded configuration without application of a voltage and is in a collapsed configuration with the application of the voltage or in a collapsed configuration without application of a voltage and in an expanded configuration with the application of the voltage, the voltage being applied via the at least one first electrode and the at least one second electrode; and
    a first electroactive polymer sub element, a second electroactive polymer sub element, a first sub electrode operatively coupled to the first electoactive polymer sub element, a second sub electrode operatively coupled to the first and second electroactive polymer sub elements, a third sub electrode operatively coupled to the second electroactive polymer sub element, wherein a first voltage difference between the first sub electrode and the second sub electrode and a second voltage difference between the second sub electrode and third sub electrode results in movement of a portion of the first and second electroactive polymer sub elements in the same direction.

2. The device of claim 1, wherein the collapsible electroactive polymer element is configured to extend around at least a portion of the core, wherein the element is covered by the membrane.

3. The device of claim 1, wherein the membrane further includes additional straightening folds to reduce membrane resistance to bending.

4. The device according to claim 1, wherein the device is configured to be inserted in an ear canal.

5. The device according to claim 4, wherein the voltage is modified to change a pressure of the device for a level of sealing the ear canal.

6. The device according to claim 1, wherein the device is configured to seal an ear canal when the device is in the expanded configuration and wherein alternating electrodes are used to move sub units of electroactive polymers.

7. The device according to claim 1, wherein the device is configured to be inserted in a pipe.

8. The device according to claim 7, wherein the device is configured to seal the pipe when the device is in the expanded or collapsed configuration.

9. The device according to claim 7, wherein the device is configured to expand up to a design pressure for sealing the pipe.

10. The device according to claim 7, wherein the voltage is modified to change a pressure of the device for sealing the pipe.

11. The device according to claim 1, wherein the collapsible electroactive polymer element forms a flange shape, wherein the flange shape moves toward the core when voltage is applied between the first and second electrodes.

12. The device of claim 1, wherein the device is wired electronic device or a wireless electronic device.

13. The device of claim 1, wherein the device is one of a wireless earpiece, a wired earpiece, an earbud, a headphone, an ear terminal, hearing aid, or a behind the ear device.

14. A device comprising:
a core;
a membrane;
at least one first electrode connected to the core;
at least one second electrode connected to the membrane;
a collapsible electroactive polymer element configured to extend from or extend around at least a portion of the core, wherein the element is in an expanded configuration without application of a voltage and is in a collapsed configuration with the application of the voltage or in a collapsed configuration without application of a voltage and in an expanded configuration with the application of the voltage, the voltage being applied via the at least one first electrode and the at least one second electrode, and wherein the device is configured to expand up to a design pressure for sealing an ear canal; and
where the membrane further includes additional straightening folds to reduce membrane resistance to bending.

15. A device, comprising:
a core;
a membrane;
at least one first electrode connected to the core;
at least one second electrode connected to the membrane;
a collapsible electroactive polymer element configured to extend from or extend around at least a portion of the core, wherein the element is in an expanded configuration without application of a voltage and is in a collapsed configuration with the application of the voltage or in a collapsed configuration without application of a voltage and in an expanded configuration with the application of the voltage, the voltage being applied via the at least one first electrode and the at least one second electrode; and
a moment arm, wherein the moment arm is operatively attached at a position along the core so that the moment arm can rotate about the position and wherein the first electrode is operatively connected to a first side of the electroactive polymer element and the second electrode is operatively attached to a second side of the electroactive polymer element so that when a voltage difference is applied between the first and second electrodes the moment arm is rotated about the position.

* * * * *